United States Patent [19]
Harz et al.

[11] Patent Number: 6,093,715
[45] Date of Patent: Jul. 25, 2000

[54] PROCESS FOR PRODUCING RIBOFLAVIN-CONTAINING GRANULES

[75] Inventors: Hans-Peter Harz, Dudenhofen; Loni Schweikert, Altrip, both of Germany; Douglas Norbert Schmidt, Grosse Ile, Mich.

[73] Assignee: BASF Aktiengesellschaft, Ludwigshafen, Germany

[21] Appl. No.: 09/275,107

[22] Filed: Mar. 24, 1999

[51] Int. Cl.$^7$ .................... A61K 31/525; C07D 475/14
[52] U.S. Cl. ................. 514/251; 514/345; 544/249; 544/251
[58] Field of Search .................. 514/345, 251; 544/249, 251

[56] References Cited

U.S. PATENT DOCUMENTS

| | | | |
|---|---|---|---|
| 4,725,427 | 2/1988 | Ashmead | 424/44 |
| 4,868,180 | 9/1989 | Izuhara et al. | 514/251 |
| 5,185,336 | 2/1993 | Caviezel et al. | 514/251 |
| 5,300,303 | 4/1994 | Grimmer et al. | 424/489 |

OTHER PUBLICATIONS

*Chem. Ing. Tech.*, 59 (1987), vol. 2, pp. 112–117.

*Primary Examiner*—John M. Ford
*Assistant Examiner*—Pavanaram V. Sripada
*Attorney, Agent, or Firm*—Keil & Weinkauf

[57] ABSTRACT

Process for producing riboflavin granules or riboflavin microgranules with a riboflavin content of from 90 to 99.5% by weight and with a particle size range from 50 to 450 μm, which entails adding during the granulation at least one auxiliary selected from the group consisting of alkali metal and alkaline earth metal halides, alkali metal and alkaline earth metal carbonates, alkali metal and alkaline earth metal bicarbonates, alkali metal and alkaline earth metal phosphates, crosslinked cellulose and cellulose derivatives and crosslinked polyvinylpyrrolidone in amounts of from 0.5 to 10% by weight, all % by weight data being based in each case on the dry product.

16 Claims, No Drawings

PROCESS FOR PRODUCING RIBOFLAVIN-CONTAINING GRANULES

The invention relates to a process for producing riboflavin-containing granules.

Riboflavin (vitamin $B_2$) is used for many purposes in the food and drugs industries as additive which is either essential or used only for coloring foodstuffs and drugs. Production thereof by synthesis or biotechnological means in some cases results in very fine-particle powders which partly consist of long yellow needles. Riboflavin in this form has very poor handling and flow properties.

The fine-particle powder inter alia produces considerable amounts of dust, has a very low bulk density (usually below 0.2 g/ml), easily acquires electrostatic charges, shows poor flow behavior and can therefore be processed further only with great difficulty. A further serious disadvantage of the fine-particle powder is that it is virtually unsuitable for producing tablets with a riboflavin content exceeding 25% by weight (cf. Bühler "Vademecum for Vitamin Formulations", Wissenschaftliche Verlags-gesellschaft, Stuttgart, pages 98 to 99).

In order to solve these problems, in the past processes for granulating riboflavin with or without granulating aids have been developed in order to obtain a product having acceptable flow and compression properties.

Thus, EP-A-0 219 276 describes riboflavin granules which contain 90 to 99% by weight of the vitamin plus a binder.

EP-A-0 457 075 describes a process for producing free-flowing, dust- and binder-free riboflavin spray granules.

Although these granules are clinically very suitable for further processing—whether for direct tableting, for producing other pharmaceutical preparations containing riboflavin or producing vitamin $B_2$-containing human and animal foods—the riboflavin release rate is frequently still unsatisfactory, especially from the tablets produced using these granules.

It is an object of the present invention to develop a process which can be used to produce in an industrially straightforward manner riboflavin granules which, on the one hand, are very suitable for further processing, for example for direct tableting, and, on the other hand, ensure a good riboflavin release rate from the tablets produced therewith.

We have found that this object is achieved by a process for producing riboflavin granules or riboflavin microgranules with a riboflavin content of from 90 to 99.5% by weight and with a particle size range from 50 to 450 $\mu$m, which comprises adding during the granulation at least one auxiliary selected from the group consisting of alkali metal and alkaline earth metal halides, alkali metal and alkaline earth metal carbonates, alkali metal and alkaline earth metal bicarbonates, alkali metal and alkaline earth metal phosphates, crosslinked cellulose and cellulose derivatives and crosslinked polyvinylpyrrolidone in amounts of from 0.5 to 10% by weight, all % by weight data being based on the dry product.

Granulation processes suitable for the purpose of the invention are in principle all methods known to the skilled worker for producing granules, particular mention being made of wet granulation. These include the granulation processes specified in EP-A-0 457 075, EP-A-0 497 177 and EP-A-0 219 276, which are based on spray drying and fluidized bed spray drying.

The process according to the invention is advantageously carried out by subjecting an aqueous or water-containing suspension, preferably a purely aqueous suspension, of riboflavin together with at least one auxiliary selected from the group consisting of alkali metal and alkaline earth metal halides, alkali metal and alkaline earth metal carbonates, alkali metal and alkaline earth metal bicarbonates, alkali metal and alkaline earth metal phosphates, crosslinked cellulose and cellulose derivatives and crosslinked polyvinylpyrrolidone to a spray drying or fluidized bed spray drying, in particular an agglomerating spray drying.

A water-containing suspension of riboflavin means, for example, a suspension of riboflavin in a not too high-boiling solvent if this solvent additionally contains water. The water content in the suspension should then be at least 10% by weight. Particularly suitable are water-miscible solvents such as $C_1$–$C_4$-alcohols.

The auxiliaries used according to the invention belong to the following classes of substances:

alkali metal and alkaline earth metal halides such as NaCl, KCl, $MgCl_2$, $CaCl_2$, NaF, KF, NaI, KI;

alkali metal and alkaline earth metal carbonates and alkali metal and alkaline earth metal bicarbonates such as $Na_2CO_3$, $K_2CO_3$, $CaCO_3$, $MgCO_3$, $NaHCO_3$, $KHCO_3$;

alkali metal and alkaline earth metal phosphates such as $Na_3PO_4$, $Ca_3(PO_4)_2$, $CaHPO_4$;

crosslinked cellulose and cellulose derivatives such as crosslinked sodium carboxymethylcellulose (from FMC Corp., USA);

crosslinked polyvinylpyrrolidone such as Kollidon® CL, Kollidon® CL-M and Crospovidon® M (BASF Aktiengesellschaft).

Preferred auxiliaires for the granules produced according to the invention are compounds selected from the group consisting of sodium chloride, potassium chloride, sodium carbonate, potassium carbonate, sodium bicarbonate, crosslinked sodium carboxymethylcellulose and crosslinked polyvinylpyrrolidone.

The procedure for granulation by spray drying generally involves spraying an aqueous or water-containing suspension of a mixture of riboflavin and at least one auxiliary selected from the group consisting of alkali metal and alkaline earth metal halides, alkali metal and alkaline earth metal carbonates, alkali metal and alkaline earth metal bicarbonates, alkali metal and alkaline earth metal phosphates, crosslinked cellulose and crosslinked polyvinylpyrrolidone in accordance with the drying rate in a spray dryer.

For this purpose, firstly at least one of the abovementioned auxiliaries is added—as solid or in the form of an aqueous suspension—to the riboflavin suspension and is mixed in with suitable stirring or dispersing machines.

The suspension with a riboflavin content of from 5 to 40% by weight, preferably 15 to 30% by weight, and a content of at least one auxiliary of from 0.05 to 4.5% by weight, preferably 0.15 to 3.5% by weight, is conveyed by a suitable pump to the atomizer of the spray tower.

The atomization in the spray tower can be carried out both with pressure nozzles, two-component nozzles or centrifugal atomizers. Pressure nozzle atomization is preferred for viscous media.

The hot gas (air or inert gas) entering the dryer to dry the atomized riboflavin droplets has an inlet temperature between 120° C. and 250° C., preferably between 150 and 200° C.

Product and gas may pass through the dryer co-currently, countercurrently, or in a mixed stream, but co-current towers are preferred.

The dried granules can then be discharged at the bottom of the dryer or be carried along by the stream of gas and deposited in a cyclone or filter.

It is particularly preferred to use a spray dryer with integrated fluidized bed as described in Chem. Ing. Tech. 59 (1987) No. 2, pages 112 to 117. This process is also referred to as agglomerating spray drying.

It is possible with this drying variant to produce, inter alia, products with improved handling properties. With this type of dryer, a fluidized bed is flanged onto the dryer and the fines from the granules are returned to the tower where the dust particles serve as agglomeration nuclei. These dryers are often referred to FSD (fluid spray dryer), SBD (spray bed dryer) or MSD (multistage dryer).

The general procedure for agglomerating spray drying, which is advantageously carried out continuously, is such that a) an aqueous suspension of a mixture of 5 to 40% by weight, preferably 15 to 30% by weight, of riboflavin and 0.05 to 4.5% by weight, preferably 0.15 to 3.5% by weight, of at least one auxiliary selected from the group consisting of alkali metal and alkaline earth metal halides, alkali metal and alkaline earth metal carbonates, alkali metal and alkaline earth metal bicarbonates, alkali metal and alkaline earth metal phosphates, crosslinked cellulose and cellulose derivatives, and crosslinked polyvinylpyrrolidone is sprayed continuously in accordance with the drying rate into the dryer, b) the dry powder which is formed as granules is collected in a fluidized bed which is attached to the dryer and is kept at 20 to 120° C., preferably at 40 to 80° C., c) the granules with a riboflavin content of from 90 to 99.5% by weight and a content of at least one of the auxiliaries mentioned under a) of from 0.5 to 10% by weight, in each case based on the dry product, are, after a suitable residence time, removed continuously from the fluidized bed, d) the removed granules are fractionated where appropriate by a suitable apparatus into particle fractions and e) the finer-particle granules and/or the finer particles obtained by grinding larger granules are returned to the spray dryer as agglomeration nuclei.

It is also possible for the fine particles carried along with the exit air and deposited in the cyclone or dust filter to be returned to the spray dryer as agglomeration nuclei.

Riboflavin granules can be produced by fluidized bed spray drying both batchwise and continuously. The continuous procedure is preferred, analogous to the agglomerating spray drying.

The general procedure for continuous fluidized bed spray drying is such that a) riboflavin is introduced in the form of a dry riboflavin powder or of spray granules or microgranules, alone or together with an auxiliary selected from the group consisting of alkali metal and alkaline earth metal halides, alkali metal and alkaline earth metal carbonates, alkali metal and alkaline earth metal bicarbonates, alkali metal and alkaline earth metal phosphates, crosslinked cellulose and cellulose derivatives and crosslinked polyvinylpyrrolidone, into a fluidized bed which is kept at 20 to 120° C., preferably 40 to 80° C., to start up the process, b) the aqueous suspension of a mixture of 5 to 40% by weight, preferably 15 to 30% by weight, of riboflavin and 0.05 to 4.5% by weight, preferably 0.15 to 3.5% by weight, of at least one auxiliary selected from the group consisting of alkali metal and alkaline earth metal halides, alkali metal and alkaline earth metal carbonates, alkali metal and alkaline earth metal bicarbonates, alkali metal and alkaline earth metal phosphates, crosslinked cellulose and crosslinked polyvinylpyrrolidone is continuously sprayed into the fluidized bed in accordance with the drying rate, c) the granules with a riboflavin content of from 90 to 99.5% by weight and a content of at least one of the auxiliaries mentioned under a) of from 0.5 to 10% by weight, in each case based on the dry product, are, after a suitable residence time, continuously removed from the fluidized bed, d) the removed granules are fractionated where appropriate by a suitable apparatus into particle fractions and e) the finer-particle granules and/or the finer particles obtained by grinding larger granules are returned to the granulation process.

The gas used to form the fluidized bed generally has an inlet temperature of from 60 to 250° C., preferably 140 to 185° C., and an outlet temperature of 40 to 140° C., preferably 60 to 85° C., resulting in temperatures of about 20 to 120° C., preferably 40 to 80° C., in particular 60 to 80° C., in the fluidized bed.

When the process is in the equilibrium state, the mass flow of required product removed from the process is as large as the mass flow of riboflavin/aid fed to the spray nozzles, on a dry matter basis.

The granulation processes according to the invention generally result—depending on the control of particle size—in the following particle size fractions:

1. about 5 to 95%, preferably 30 to 70%, in the particle size range up to 100 $\mu$m,
2. about 25 to 85%, preferably 30 to 70%, in the particle size range from 100 to 300 $\mu$m,
3. about 1 to 30% in the particle size range >300 $\mu$m, where the three particle size fractions add up to 100%.

The properties of the final product are influenced not only by the drying process but also by the shape and size of the riboflavin crystals.

For the agglomeration process it is advantageous for the average crystal size to be between 0.1 and 10 $\mu$m, preferably 0.3 and 5 $\mu$m, particularly preferably between 0.5 and 3 $\mu$m. The appropriate crystal size can be achieved by grinding, preferably wet grinding, of the riboflavin suspension, for example using agitator cone mills. In this case, the suspension is pumped cyclically or in transit through the mill. The rotating agitators in the mill generate the shear stress between material to be milled and the milling elements. To avoid abrasion of the milling elements, it is sensible to use particularly hard milling elements (e.g. yttrium-stabilized ceramic milling elements).

The invention also relates to riboflavin granules or riboflavin microgranules containing from 90 to 99.5% by weight, preferably 93 to 99% by weight, of riboflavin and from 0.5 to 10% by weight, preferably 1 to 7% by weight, of at least one auxiliary selected from the group consisting of alkali metal and alkaline earth metal halides, alkali metal and alkaline earth metal carbonates, alkali metal and alkaline earth metal bicarbonates, alkali metal and alkaline earth metal phosphates, crosslinked cellulose and cellulose derivatives and crosslinked polyvinylpyrrolidone, where the % by weight data are based in each case on the dry product.

The preferred riboflavin granules or riboflavin microgranules comprise at least one auxiliary selected from the group consisting of sodium chloride, potassium chloride, sodium carbonate, potassium carbonate, sodium bicarbonate, crosslinked sodium carboxymethylcellulose and crosslinked polyvinylpyrrolidone, and the particle size range of the fine-particle riboflavin is from 50 to 450 µm, preferably 100 to 300 µm.

The riboflavin granules or riboflavin microgranules according to the invention are advantageously suitable for producing solid pharmaceutical presentations (dosage forms), preferably tablets, especially those produced by direct tableting processes.

The invention thus also relates to solid presentations comprising the abovementioned riboflavin granules according to the invention. These include tablets, microtablets, coated tablets, pastilles, capsules or pellets, preferably tablets or micro-tablets, particularly preferably direct-tabletted riboflavin.

The riboflavin content in the tablets is in the range from 1 to 100 mg, preferably 5 to 75 mg, particularly preferably in the range from 5 to 50 mg.

It is, of course, also possible to add other auxiliaries to produce the solid presentations.

These may be, inter alia:

Bulking agents and binders such as lactose, calcium phosphates, cellulose and cellulose derivatives, starch and starch derivatives, partially hydrolyzed polyvinyl acetate, sugar alcohols, sugars, fats, waxes;

disintegrants such as Kollidon® CL (from BASF), Na carboxymethyl starch, Na carboxymethylcellulose;

glidants and lubricants such as Mg stearate, Ca behenate, stearic acid, PEG;

flow regulators such as highly disperse silica;

film formers such as polyacrylates and polymethacrylates (Eudragit types), copolymers based on acrylate derivatives, hydroxypropylmethylcellulose, hydroxypropylcellulose, cellulose acetate, cellulose acetate phthalate and other enteric coating materials;

humectants such as glycerol, propylene glycol, sorbitol, mannitol, polyethylene glycols and plasticizers, colors, surfactants, salts, dispersing aids.

The solid pharmaceutical presentations (dosage forms) produced using the riboflavin-containing granules according to the invention are distinguished inter alia by a high in vitro riboflavin release rate. Thus, the release rate measured by the USP XXII paddle method is at least 75% by weight of riboflavin, preferably more than 80% by weight, particularly preferably 83 to 95% by weight, of riboflavin after 60 min.

The following examples explain in detail the production and use of the riboflavin granules according to the invention.

Production of riboflavin-containing granules

EXAMPLE 1

A 20% by weight aqueous riboflavin suspension was ground by a ball mill to an average particle size of 1 µm, mixed with 5% by weight NaHCO$_3$ (based on the total solids content) and homogenized. The suspension was then sprayed in an FSD dryer (Niro, type 12,5) under 130 bar. The inlet temperature of the drying gas in the spraying tower was 190° C., and the tower outlet temperature was 60° C. The inlet air temperature for the internal fluidized bed was likewise 60° C. The fines were deposited in a 40 m$^2$ tubular filter and were returned to the spray tower. The microgranules produced in this way had a water content of less than 1.5% by weight and an average particle size of about 120 µm.

EXAMPLES 2 to 4

Riboflavin granules which, besides 95% by weight riboflavin, contained 5% by weight of the following auxiliaries (the % by weight data are based in each case on the dry product) were produced as in Example 1:

Example 2:
  5% by weight NaCl,
  average particle size: 110 µm;
Example 3:
  5% by weight Kollidon® CL-M (from BASF Aktiengesellschaft)
  average particle size: 120 µm;
Example 4:
  5% by weight AcDiSol® (from FMC Corp.)
  average particle size: 115 µm.

EXAMPLE 5

A 17% by weight aqueous riboflavin suspension was ground in a ball mill to an average particle size of 2 µm, mixed with 5% by weight of crosslinked Na carboxymethylcellulose (based on the total solids content) and homogenized. The suspension was then atomized in a laboratory spray dryer (from Niro, type Minor) with a two-component nozzle under 4 bar. The tower inlet temperature was 190° C., and the tower outlet temperature was 62° C. The riboflavin powder was deposited from the drying air in a cyclone. The powder produced in this way had a water content of 0.5% by weight and an average particle size of 70 µm.

Production of riboflavin-containing tablets

EXAMPLES 6 to 9

266.7 g of lactose (Tablettose®, from Meggle), 134.3 g of micro-crystalline cellulose (Avicel® PH 102, from FMC), 10 g of highly disperse SiO$_2$ (Aerosil®, from Degussa) and 2.5 g of crosslinked Na carboxymethylcellulose (AcDiSol®, from FMC Corp.) were homogenized for 10 minutes and passed through a sieve with a mesh width of 0.8 mm. Then 3.3 g of magnesium stearate and 83.3 g of riboflavin granules produced by one of Examples 1 to 4 were added, and the mixture was homogenized anew. The finished tablet mixture was compressed to 8 mm tablets in a Korsch PH 106 rotary tableting press at a tableting rate of 20 rpm under a force of 10 kN.

Tablet composition:
  50 mg of vitamin B$_2$ with auxiliary shown in Table 1
  160 mg of Tablettose®
  80.5 mg of Avicel® PH 102
  1.5 mg of AcDiSol®
  6.0 mg of Aerosil®
  2.0 mg of Mg stearate

EXAMPLE 10

266.7 g of Tablettose®, 134.3 g of Avicel® PH 102, 10 g of Aerosil® and 2.5 g of AcDiSol® were homogenized for 10 minutes and passed through a sieve with a mesh width of 0.8 mm. Then 3.3 g of magnesium stearate and 83.3 g of riboflavin granules produced as in Example 5 were added and the mixture was homogenized anew. The finished tablet mixture was compressed to 8 mm tablets in a Korsch PH 106 rotary tableting press at a tableting rate of 20 rpm under a force of 10 kN.

Tablet composition:
  50 mg of vitamin B$_2$ with auxiliary shown in Table 1
  160 mg of Tablettose®

80.5 mg of Avicel® PH 102

1.5 mg of AcDiSol®

6.0 mg of Aerosil®

2.0 mg of Mg stearate

EXAMPLE 11 (Comparative Example)

266.7 g of Tablettose® (from Meggle), 134.3 g of Avicel® PH 102 (from FMC) and 10 g of Aerosil® (from Degussa) and 2.5 g of crosslinked cellulose (AcDiSol®, from FSM) were homogenized for 10 minutes and passed through a sieve with a mesh width of 0.8 mm. Then 3.3 g of magnesium stearate and 83.3 g of riboflavin granules (produced as in Example 1 but without adding an auxiliary) were added and the mixture was homogenized anew. The finished tablet mixture was compressed to 8 mm tablets in a Korsch PH 106 rotary tablet press at a tableting rate of 20 rpm under a force of 10 kN.

Tablet composition:

50 mg of vitamin $B_2$ without auxiliary 160 mg of Tablettose®

80.5 mg of Avicel® PH 102

1.5 mg of AcDiSol®

6.0 mg of Aerosil®

2.0 mg of Mg stearate

The riboflavin release rate from the tablets produced as in Examples 6 to 11 was measured by the dissolution test of USP XXII in 900 ml of 1.0 N HCl at 75 rpm and 37° C. with UV detection at 267 nm.

The value indicated for the release in Table 1 represents the release of riboflavin after only 30 min to differentiate the measurements better.

TABLE 1

| Tablet of Example | Auxiliary | Release rate (after 30 min) |
|---|---|---|
| 6 | NaHCO$_3$ | 86% |
| 7 | NaCl | 83% |
| 8 | Kollidon ® CL | 88% |
| 9 | AcDiSol ® | 86% |
| 10 | AcDiSol ® | 88% |
| 11 (Comparison) | — | 75% |

We claim:

1. A process for producing riboflavin granules or riboflavin microgranules with a riboflavin contend of from 90 to 99.5% by weight and with a particle size range from 50 to 450 μm, which comprises adding during the granulation at least one auxiliary selected from the group consisting of alkali metal and alkaline earth metal halides, alkali metal and alkaline earth metal carbonates, alkali metal and alkaline earth metal bicarbonates, alkali metal and alkaline earth metal phosphates, crosslinked cellulose and cellulose derivatives and crosslinked polyvinylpyrrolidone in amounts of from 0.5 to 10% by weight, all % by weight data being based in each case on the dry product.

2. A process as claimed in claim 1 using from 0.5 to 10% by weight of at least one auxiliary selected from the group consisting of sodium chloride, potassium chloride, sodium carbonate, potassium carbonate, sodium bicarbonate, crosslinked sodium carboxymethylcellulose and crosslinked polyvinylpyrrolidone.

3. A process as claimed in claim 1, wherein an aqueous suspension containing from 5 to 40% by weight of riboflavin and from 0.05 to 4.5% by weight of said at least one auxiliary as defined in either of claims 1 or 2 is subjected to a spray drying or fluidized bed spray drying.

4. A process as claimed in claim 3, wherein the spray drying or fluidized bed spray drying comprises a continuous process.

5. A process as claimed in claim 4, wherein the spray drying comprises a continuous agglomerating spray drying in which a) an aqueous suspension of a mixture of riboflavin and at least one auxiliary selected from the group consisting of alkali metal and alkaline earth metal halides, alkali metal and alkaline earth metal carbonates, alkali metal and alkaline earth metal bicarbonates, alkali metal and alkaline earth metal phosphates, crosslinked cellulose and cellulose derivatives, and crosslinked polyvinylpyrrolidone is sprayed continuously in accordance with the drying rate into the dryer, b) the dry powder which is formed as granules is collected in a fluidized bed which is attached to the dryer and is kept at 20 to 120° C., c) the granules with a riboflavin content of from 90 to 99.5% by weight and a content of at least one of the auxiliaries mentioned under a) of from 0.5 to 10% by weight, in each case based on the dry product, are, after a suitable residence time, removed continuously from the fluidized bed, d) the removed granules are fractionated where appropriate by a suitable apparatus into particle fractions and e) the finer-particle granules and/or the finer particles obtained by grinding larger granules are returned to the spray dryer as agglomeration nuclei.

6. A process as claimed in claim 4, wherein the continuous fluidized bed spray drying is carried out by a) riboflavin being introduced in the form of a dry riboflavin powder or of spray granules or microgranules, alone or together with an auxiliary selected from the group consisting of alkali metal and alkaline earth metal halides, alkali metal and alkaline earth metal carbonates, alkali metal and alkaline earth metal bicarbonates, alkali metal and alkaline earth metal phosphates, crosslinked cellulose and cellulose derivatives and crosslinked polyvinylpyrrolidone, into a fluidized bed which is kept at 20 to 120° C. to start up the process, b) the aqueous suspension of a mixture of riboflavin and of at least one auxiliary selected from the group consisting of alkali metal and alkaline earth metal halides, alkali metal and alkaline earth metal carbonates, alkali metal and alkaline earth metal bicarbonates, alkali metal and alkaline earth metal phosphates, crosslinked cellulose and cellulose derivatives and crosslinked polyvinylpyrrolidone being continuously sprayed into the fluidized bed in accordance with the drying rate, c) the granules with a riboflavin content of from 90 to 99.5% by weight and a content of at least one of the auxiliaries mentioned under a) of from 0.5 to 10% by weight, in each case based on the dry product, being, after a suitable residence time, continuously removed from the fluidized bed, d) the removed granules being fractionated where appropriate by a suitable apparatus into particle fractions and e) the finer-particle granules and/or the finer particles obtained by grinding larger granules being returned to the granulation process.

7. A process as claimed in claim 1, wherein said riboflavin has a particle size of from 0.1 to 10 μm before said granulation.

8. Riboflavin granules or riboflavin microgranules containing from 90 to 99.5% by weight of riboflavin and from 0.5 to 10% by weight of at least one auxiliary selected from the group consisting of alkali metal and alkaline earth metal halides, alkali metal and alkaline earth metal carbonates, alkali metal and alkaline earth metal bicarbonates, alkali metal and alkaline earth metal phosphates, crosslinked cellulose and cellulose derivatives and crosslinked polyvinylpyrrolidone, where the % by weight data are based in each case on the dry product.

9. Riboflavin granules or riboflavin microgranules as claimed in claim 8, comprising at least one auxiliary selected from the group consisting of sodium chloride, potassium chloride, sodium carbonate, potassium carbonate, sodium bicarbonate, crosslinked sodium carboxymethylcellulose and crosslinked polyvinylpyrrolidone.

10. Riboflavin granules or riboflavin microgranules as claimed in claim 8 which have a particle size range from 50 to 450 μm.

11. Solid pharmaceutical dosage forms produced from riboflavin granules or riboflavin microgranules as defined in claim 8.

12. A process of producing tablets comprising riboflavin granules or riboflavin microgranules as claimed in claim 8, which process comprised compressing said granules or microgranules in a tablet press.

13. A tablet comprising riboflavin granules or riboflavin microgranules produced by the process of claim 12.

14. A tablet as claimed in claim 13 with a riboflavin content of from 1 to 100 mg.

15. A tablet as claimed in claim 14 with an in vitro release rate by the USP XXII method of at least 75% by weight of riboflavin after 60 min.

16. The product of the process of claim 1.

* * * * *

UNITED STATES PATENT AND TRADEMARK OFFICE
CERTIFICATE OF CORRECTION

PATENT NO. : 6,093,715
DATED : July 25, 2000
INVENTOR(S) : Harz et al.

It is certified that error appears in the above-identified patent and that said Letters Patent is hereby corrected as shown below:

<u>Column 7,</u>
Line 48, "contend" should be -- content --.
Line 50, after "adding" insert -- prior to --; after "granulation" insert -- of riboflavin --.

Signed and Sealed this

Seventh Day of August, 2001

*Attest:*

NICHOLAS P. GODICI
*Attesting Officer*     Acting Director of the United States Patent and Trademark Office